US00PP21930P3

(12) United States Plant Patent

Bautista et al.

(10) Patent No.: US PP21,930 P3

(45) Date of Patent: May 24, 2011

(54) *CAMPANULA* PLANT NAMED 'BLUE ANGEL'

(50) Latin Name: *Campanula×haylodgensis Hort.*
Varietal Denomination: Blue Angel

(75) Inventors: Emilio V. Bautista, Half Moon Bay, CA (US); Lilia Rodriguez, Half Moon Bay, CA (US)

(73) Assignee: Bay City Flower Company, Inc., Half Moony Bay, CA (US)

( * ) Notice: Subject to any disclaimer, the term of this patent is extended or adjusted under 35 U.S.C. 154(b) by 0 days.

(21) Appl. No.: 12/384,083

(22) Filed: Mar. 31, 2009

(65) Prior Publication Data

US 2010/0251449 P1 Sep. 30, 2010

(51) Int. Cl.
*A01H 5/00* (2006.01)

(52) U.S. Cl. ..... Plt./414

(58) Field of Classification Search ..... Plt./414
See application file for complete search history.

*Primary Examiner* — Kent L Bell

(74) *Attorney, Agent, or Firm* — Charles R. Cypher; James R. Cypher

(57) ABSTRACT

A plant variety of the Campanulaceae family, having the varietal designation 'Blue Angel', with a spreading growth habit, showy appearance from many blooms, and large campanulate, actinomorphic flowers. Flowers are R.H.S. 91 A (violet-blue group).

6 Drawing Sheets

Latin name of genus and species of the plant claimed: The new plant is *Campanula×haylodgensis Hort.*

Varietal denomination: The new plant's varietal denomination is 'Blue Angel'.

BACKGROUND OF THE INVENTION

The present invention relates to a new and distinct variety of the Campanulaceae family. The new variety is named 'Blue Angel'.

SUMMARY OF THE INVENTION

The distinguishing characteristics of the new variety are retained by asexually reproduced, successive generations.

The plant is a found, mutant, whole plant sport of *Campanula×hayodensis Hort.* 'Blue Rose'. The plant was found by the inventor in a cultivated area in a commercial nursery.

The new variety possesses the commercially desirable characteristics of: a spreading growth habit with dense foliage, and it produces many relatively large flowers that at maturity are R.H.S. 91 A (violet-blue group).

The new variety differs from its parent and other related cultivars by virtue of its large flowers.

The inventor has asexually reproduced the new variety through three successive generations by cuttings at a commercial nursery in Half Moon Bay Calif., and has found that the combination of characteristics as herein disclosed remain firmly fixed.

BRIEF DESCRIPTION OF THE DRAWING

The accompanying drawings serve, by color photographic means, to illustrate the new plant variety. The colors are represented as truly as possible using conventional photographic procedures.

DETAILED DESCRIPTION OF THE NEW VARIETY

Figure 1:
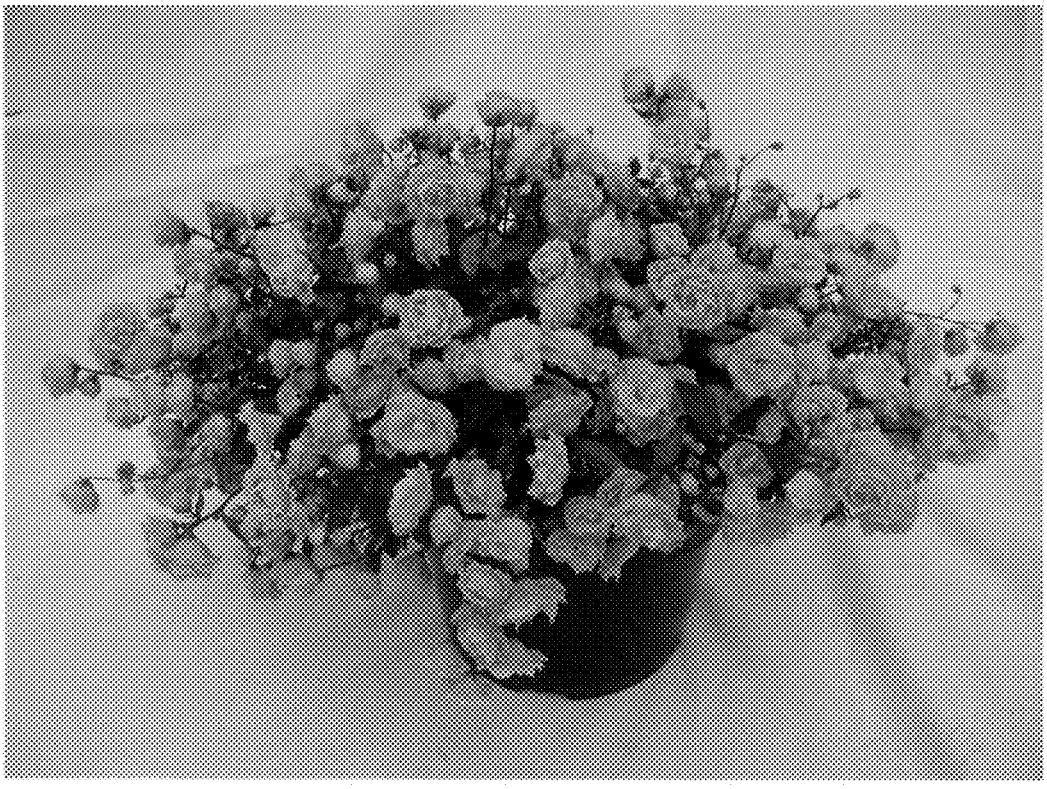
FIG. 1 is a color photograph of a plant grown from a cutting in one pot of the new variety illustrating the overall appearance and form of the plant, and the abundance of blooms.
Figure 2:
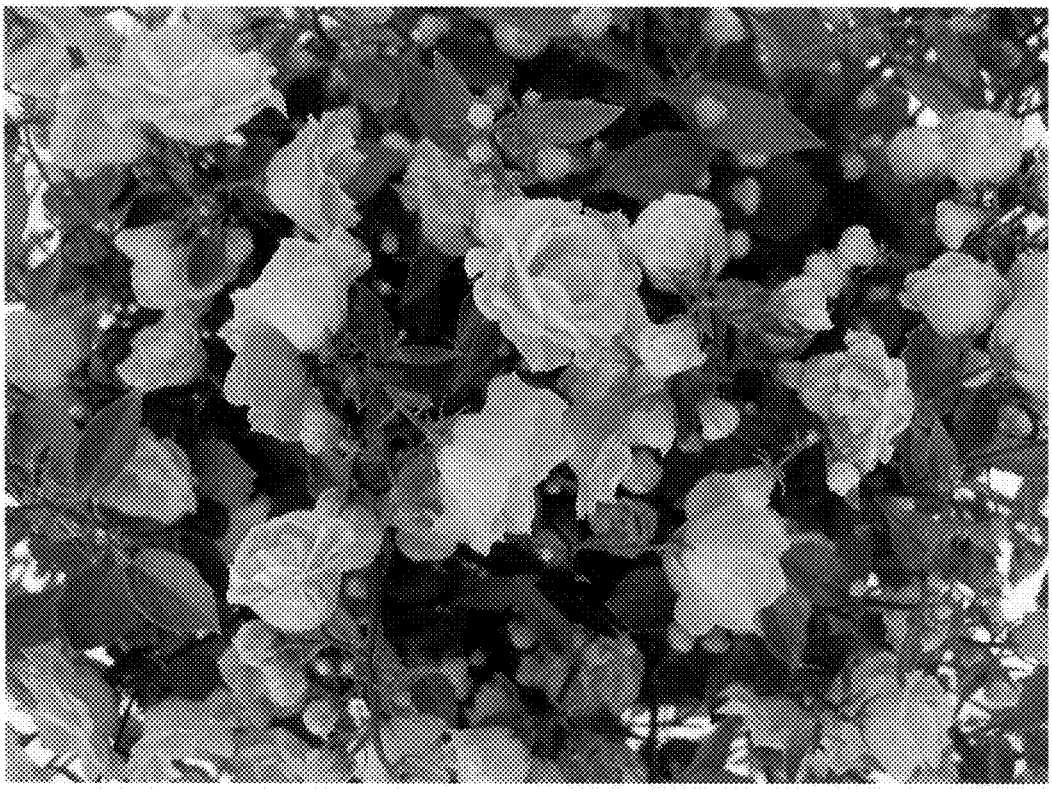
FIG. 2 is a color photograph of a number of flowers of the new variety.
Figure 3:
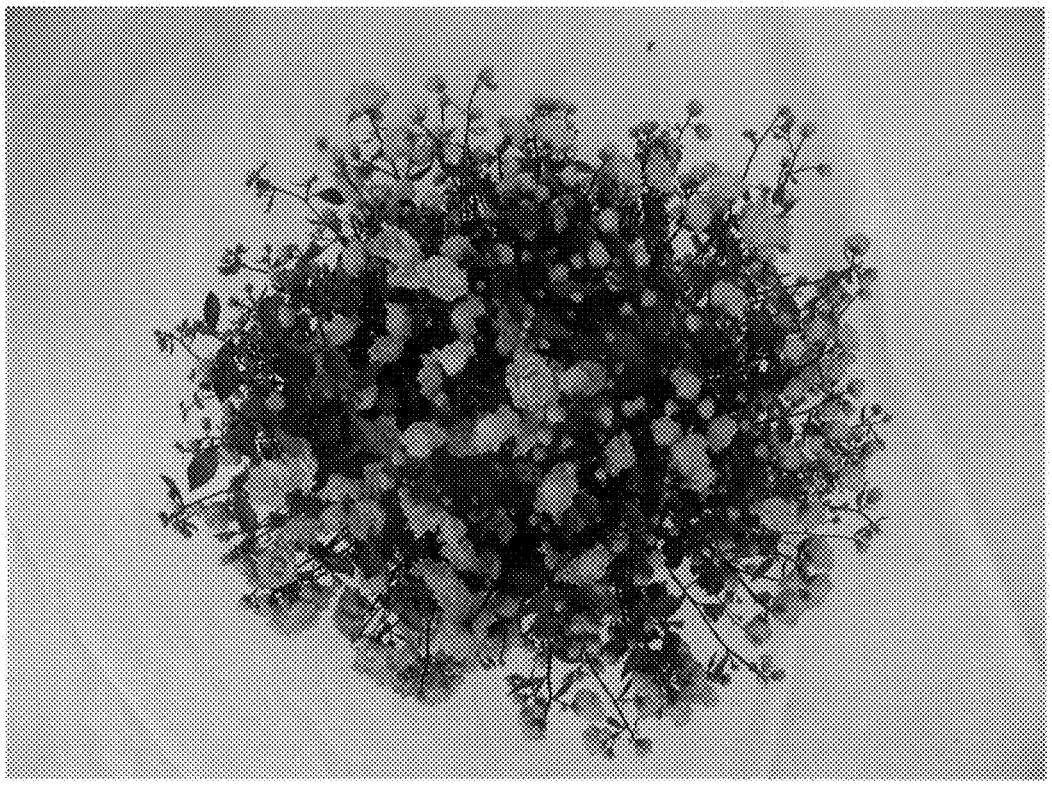
FIG. 3 is a color photograph of the plant showing the top of the plant.
Figure 4:
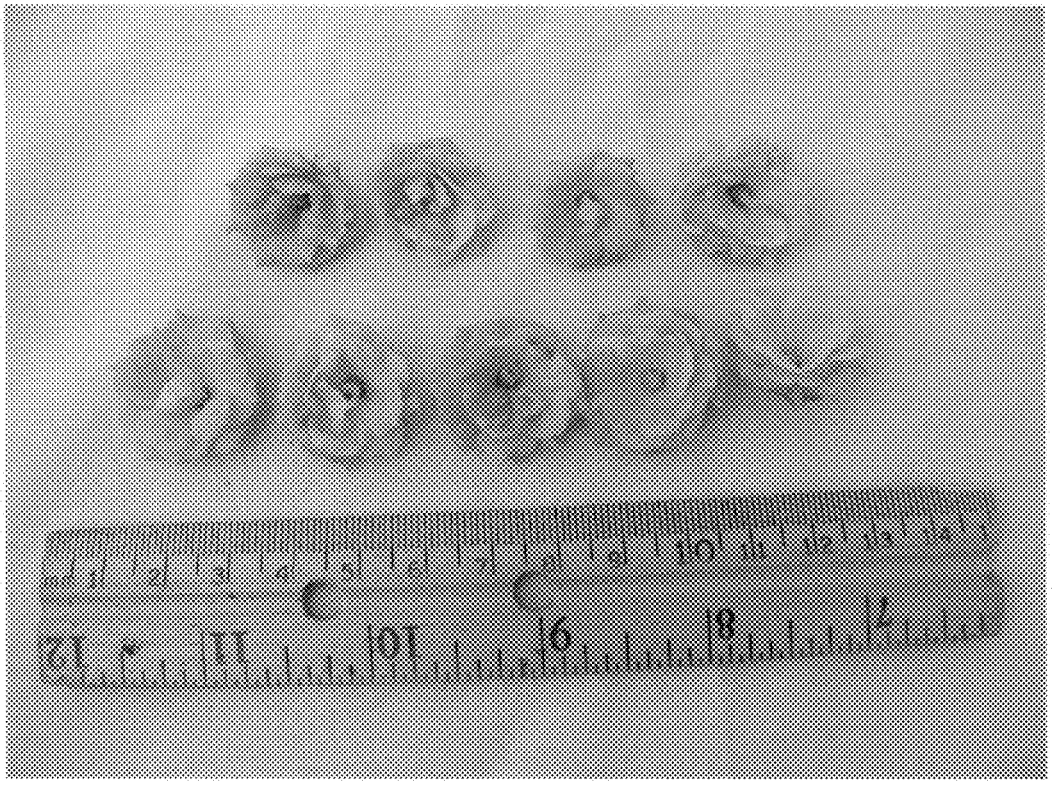
FIG. 4 is a color photograph of various flowers removed from the plant.
Figure 5:
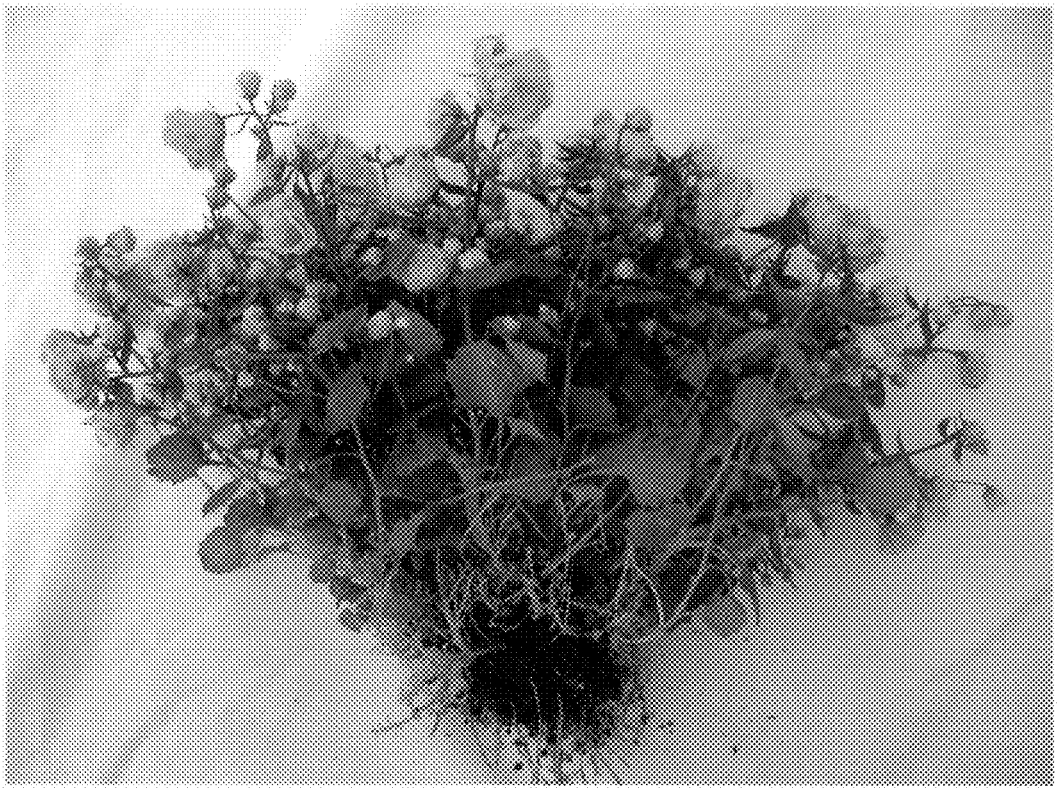
FIG. 5 is a color photograph of a plant removed from its soil.
Figure 6:
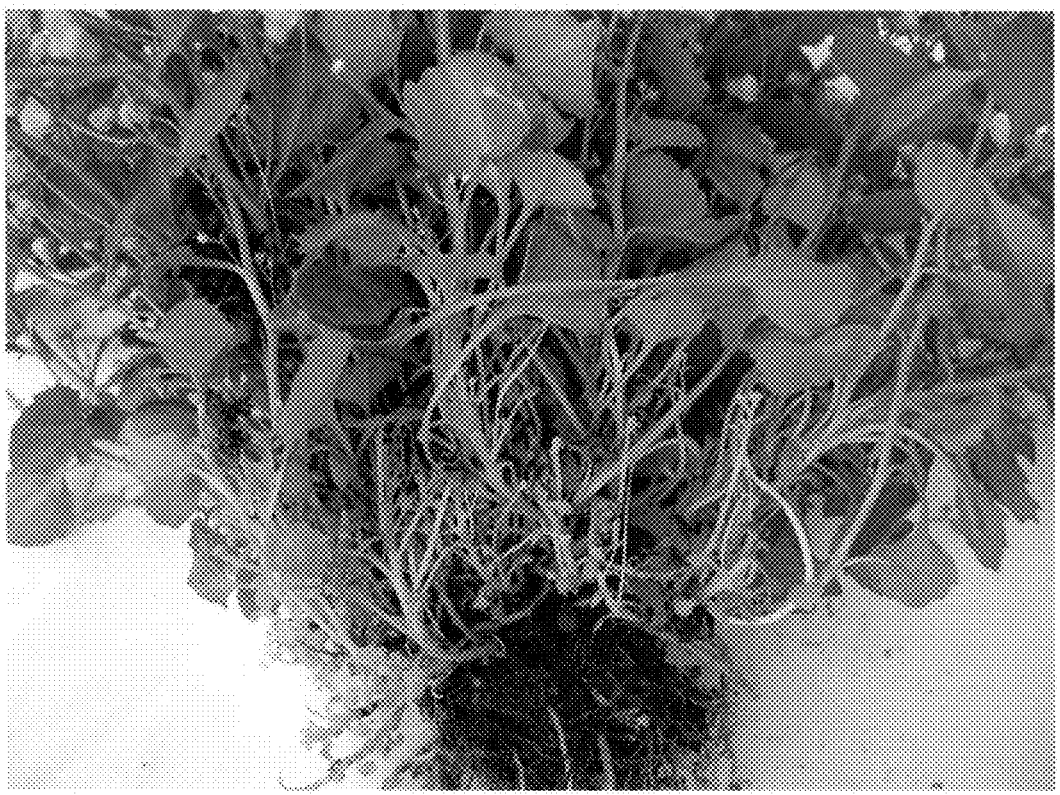
FIG. 6 is a color photograph of the base of a plant removed from its soil.
Figure 7:
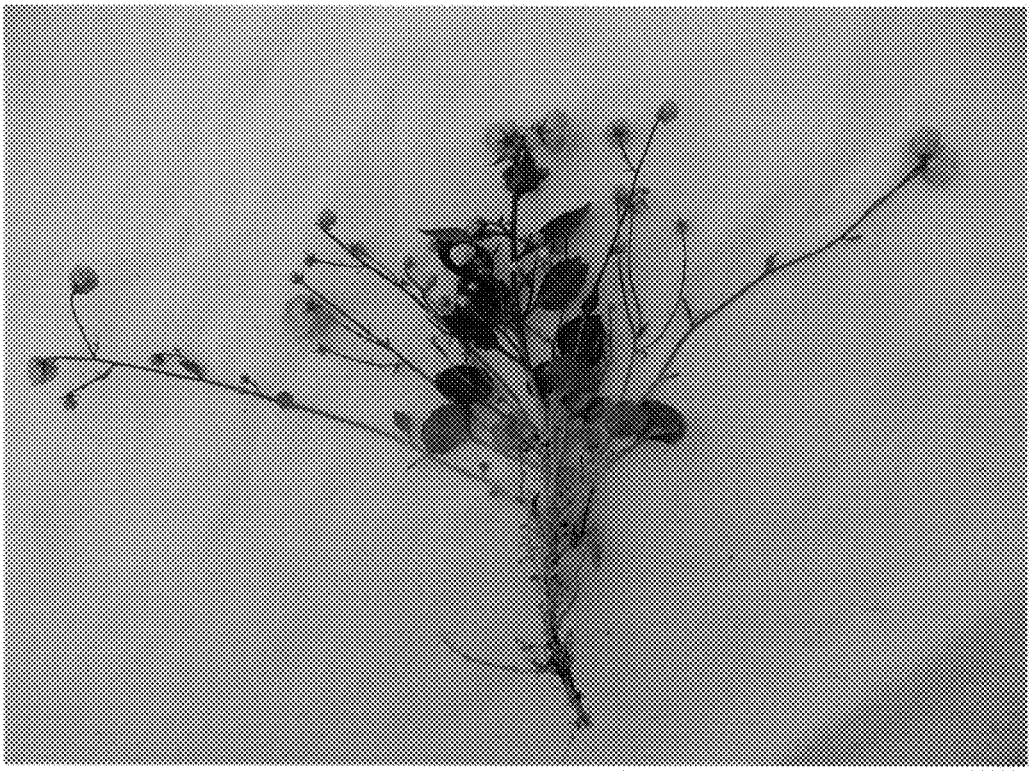
FIG. 7 is a color photograph of a single main stem of the new variety.
Figure 8:
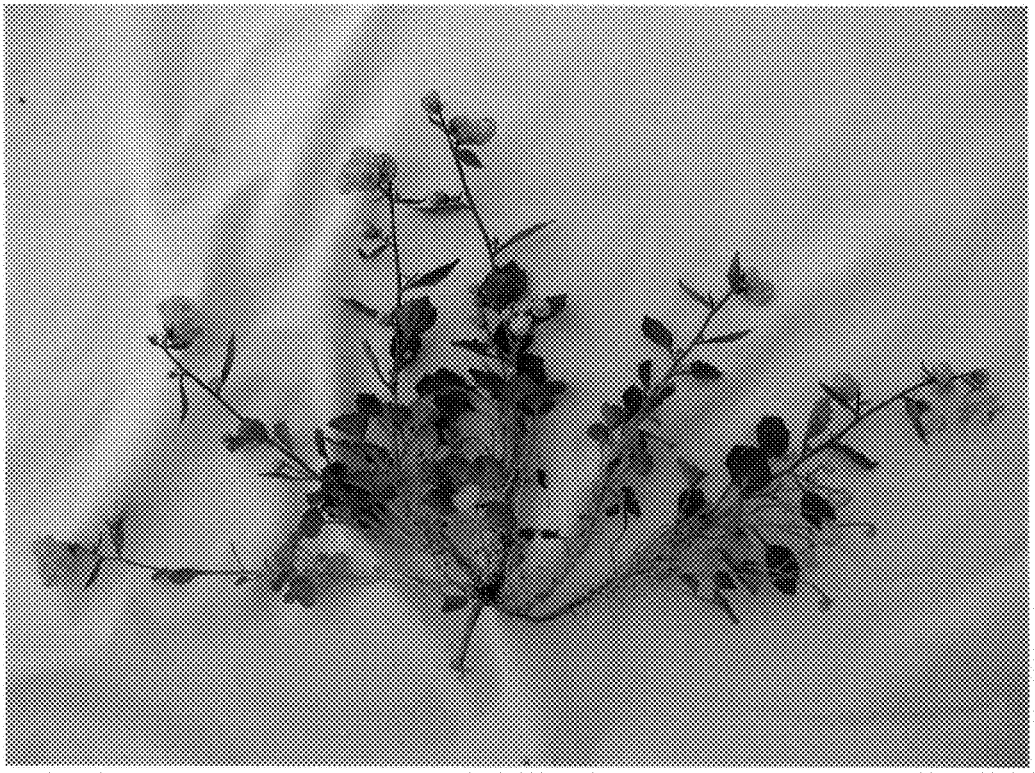
FIG. 8 is a color photograph of a single main stem of the new variety.
Figure 9:
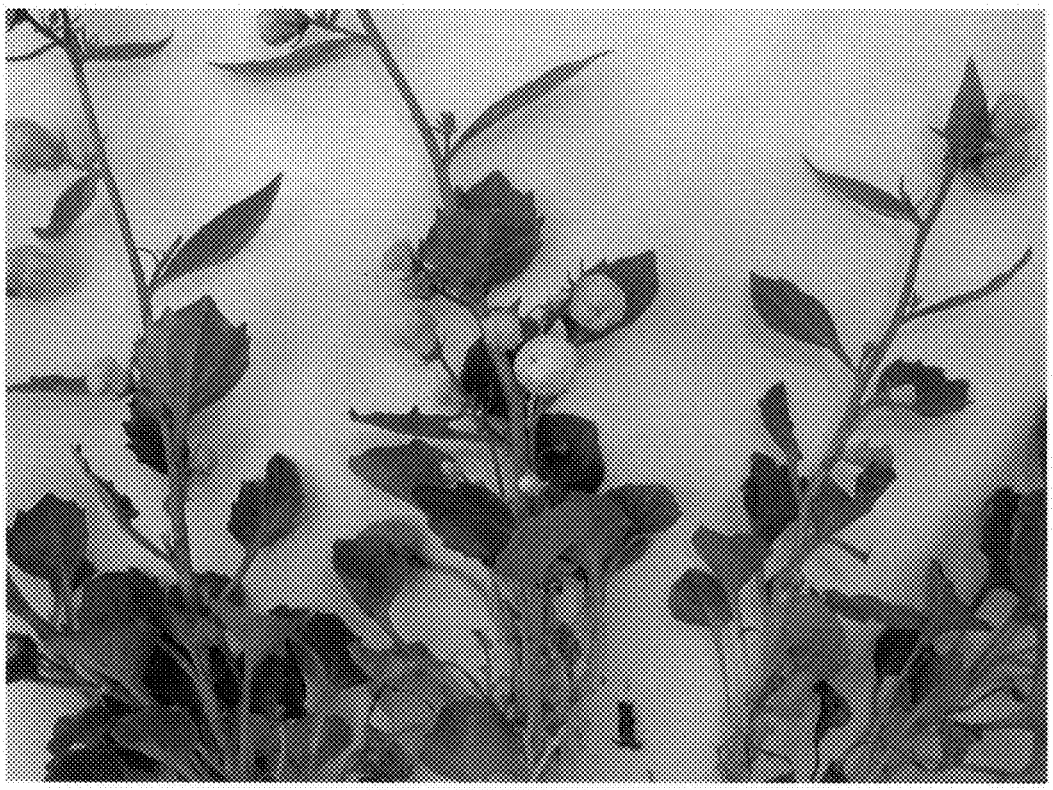
FIG. 9 is a close-up, color photograph of a single stem of the new variety, showing buds of the new variety.
Figure 10:
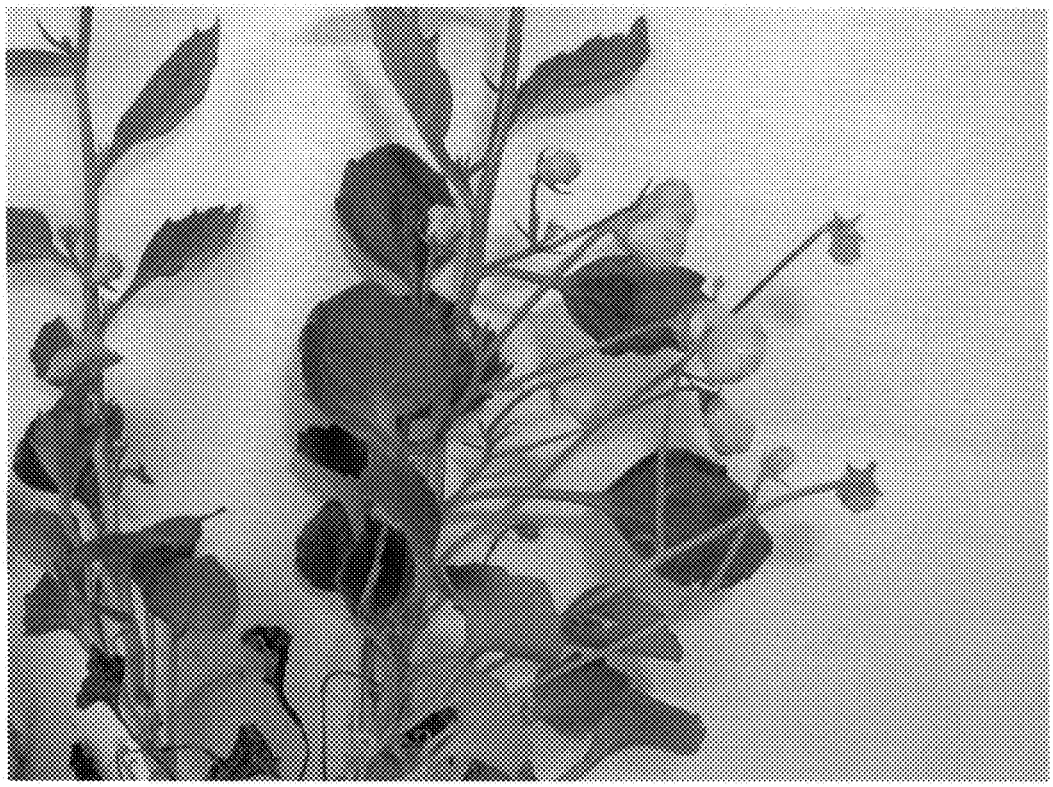
FIG. 10 is a close-up, color photograph of a single stem of the new variety, showing buds of the new variety.
Figure 11:
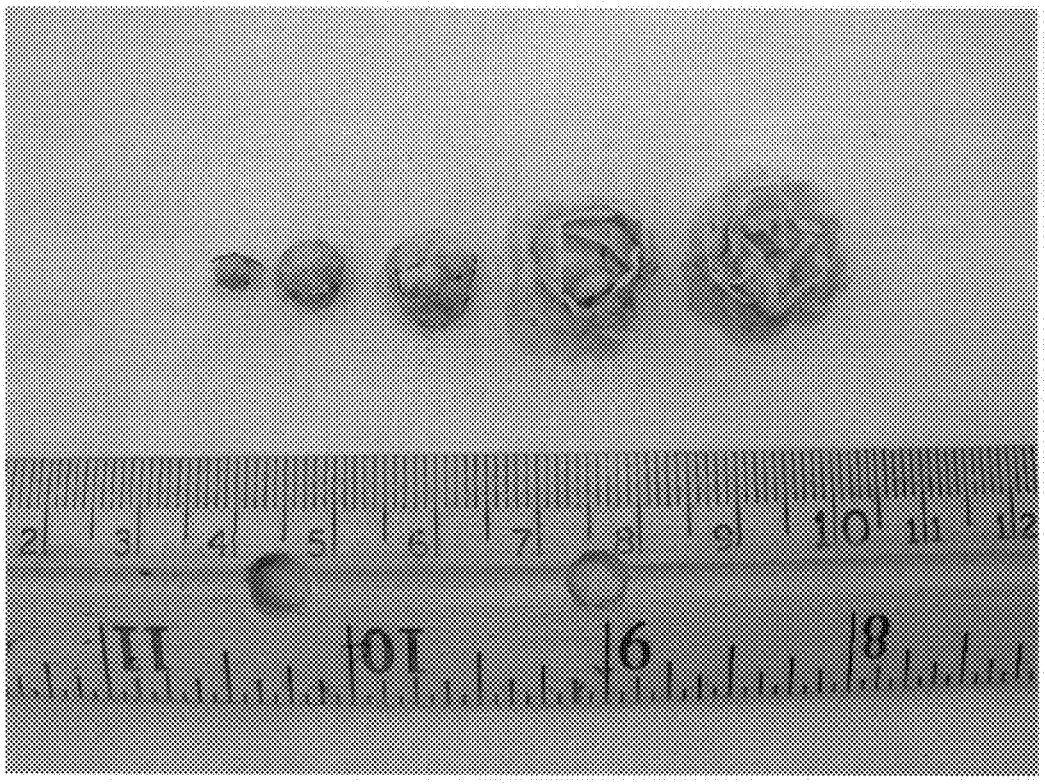
FIG. 11 is a color photograph of various buds and flowers removed from the plant.
Figure 12:
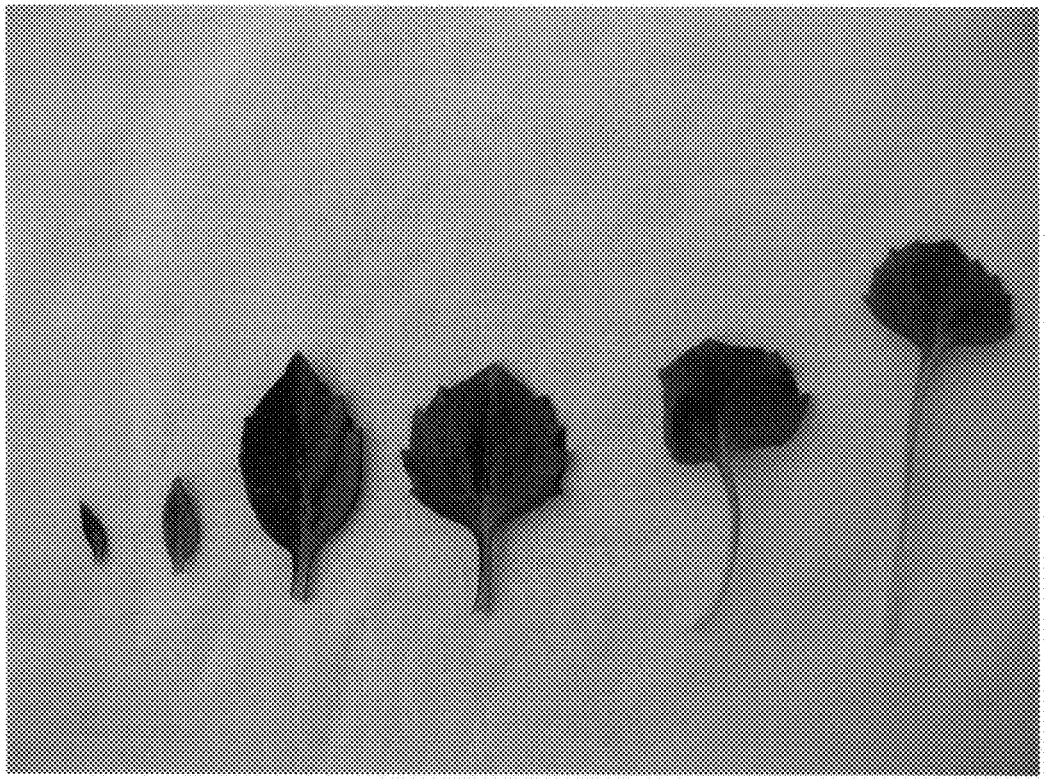
FIG. 12 is a color photograph of various leaves removed from the plant.

The following is a detailed description of the new variety. The new variety has not been observed under all possible environmental conditions. Color designation and other values stated may deviate slightly from the stated values from flowering to flowering, but the deviations will be within the range expected from varying environmental, seasonal and cultural conditions. Color designations were made according to The R.H.S. Colour Chart published by The Royal Horticultural Society of London, England.

The pictured plant was grown in a 6 inch pot.

The following description is based on observations of optimally fertilized plants grown at a commercial nursery in Half Moon Bay, Calif. Temperatures in Half Moon Bay on average range from 55 to 65 degrees Fahrenheit in the summer months, and from 45 to 55 degrees Fahrenheit in the winter months.

DETAILED PLANT DESCRIPTION

Varietal name: 'Blue Angel'.

Classification: Family—Campanulaceae. Genus and Species—*Campanula×haylodgensis Hort.*

Form: Herbaceous, terrestrial plant with many spreading lateral stems. Lateral stems are many branched with the plant spreading well away from its pot. The observed plants were approximately 17 cm high. Stems can range from 15 cm to 20 cm in length. Plant grown in a 6" pot that is ready for commercial sale has a diameter of 50 cm.

Stems:

*General.*—Stems are many branched with new shoots growing in leaf interfaces. Lateral branches that are relatively long when compared to the main stem usually start at the $11^{th}$ or 13th node below the terminal flower. Each lateral branch and each branch from a lateral branch ends in a terminal flower giving the plant a showy appearance. Node length is variable.

*Size.*—Width — 1 mm at base of flowers and as much as 2 mm wide where lateral stems have grown from main stem.

*Color.*—The upper, non-woody portions of the main stems are R.H.S. 146A (yellow-green group). The middle portions of the stems and new stems are R.H.S. 145A (yellow-green) group. Woody portions of stems are 164 B (greyed-orange group).

*Texture.*—Glabrous in upper and mid portions and woody at base.

Leaves:

*General.*—Leaves are whorled on the stem. Very young leaves are simple, lanceolate, with margins that are entire, although somewhat serrilate near the apex, the apex is acute, and the very young leaves have a relatively smaller petiole than older leaves. Mature leaves have broadly acute apexes, rounded to truncate bases, and are serrate and ovate, with relatively petioles. Leaves are pinnately veined.

*Size.*—Length — Mature leaves that are approximately 10 nodes below the meristem of the lateral branch are approximately 33 mm long, including the petiole. The petiole on these leaves is approximately 16 mm long and the blade is 17 mm long. Leaves closer to the stem's terminal infloresence lack petioles or have reduced petioles. Leaves even farther down the stem than 10 nodes can have a petiole that is 30 mm long with a blade that is 13 mm long and 15 mm wide. Width — Mature leaves are approximately 15 to 22 mm wide.

*Color.*—Adaxial surfaces of leaf and the petiole are predominately R.H.S. 147 A (yellow-green group), while the abaxial surfaces of the leaf and petiole are predominantly R.H.S. 147 B (yellow-green group).

*Texture.*—Abaxial surfaces of the leaves and petioles are glabrous. Adaxial surfaces of the leaves are glabrous.

Flowers:

*General.*—Flowers are actinomorphic, solitary on cymes, with three or four mature flowers at the top of each cyme with many younger buds farther down on the stem/inflorescence when the plant is ready for commercial sale. There is no beginning of the infolorescence and thus no discinct peduncle. Pedicels, carrying the solitary terminal flowers are glabrous and R.H.S. 146A (yellow-green group), 1 mm in width and vary in length from 5 mm to 25 mm. Flowers are also perfect, terminal and 5-lobed. The calyx is united. The corrola is campanulate with many whorls of petals. The stamens have wings. Buds are campanulate and R.H.S. 147 B (yellow-green group). Buds that are almost ready to open are 7 mm in diameter and 7 mm high. Plants are easily forced to bloom in the summer in Half Moon Bay, Calif.

*Sepals.*—General: The calyx is 5-lobed, regular and united to the ovary, and lanceolate with acute apexes and entire margins. Size: Length — 4 mm from base to tip of sepals when corrolla is 14 mm long and flower is mature. Width — 2 mm at base. Color: R.H.S. 147 A (yellow-green group) on both the abaxial and adaxial surfaces. Texture: few small white hairs.

*Petals.*—General: Petals inserted on ovary and form 5-lobed somewhat bell-shaped flower with multiple whorls (4). Corrola is campanulate. Petals are fused at their base but can be considered to be approximately 15 mm in width and 15 mm in height. Petals are broadly acute at their apex. Size of Flower (at full bloom): Height of flower — 14 mm. Diameter of flower — 22 mm. Color: Mature flowers are R.H.S. 91A (violet-blue group) on both abaxial and adaxial surfaces. The adaxial surfaces of the petals have less pigmentation at the base of the petals and more pigmentation at the tips. The pigmentation of the abaxial surface of the petals is more even. Outermost petals of the flower, when the flower is still immature, are R.H.S. 145 C (yellow-green group) on both abaxial and adaxial surfaces and develop pigmentation as the flower matures. Texture: Succulent. Glabrous when mature.

*Androecium* (*stamens*).—General: 2 to 5 inserted stamens having basal winged filaments that cover and hide the ovary. Anthers become desiccated. Stamens and anthers are often not fully formed and not uniform. Total length of stamens is typically 10 mm long. Color — Wings and filament are white R.H.S. 155D (white group). Texture — Glabrous, but with short hairs on the wings. Anther: Shape — Rod shaped, if formed. Color — Sometimes tips of filaments, where anthers would be, if present, can be R.H.S. 91A (violet-blue group).

*Gynoecium* (*pistil*).—General: Compound, parietal placentation with united style. Style: General — Inserted in top of ovary. Shape — Elongated. Usually 2 to 3 mm longer than stamens that have anthers. Color — R.H.S. 155 D (white group). Stigma: General — Inserted at maturity and erect, if it exists, generally with 1 lobe that is reflexed. Stigma is usually withered by the time the flower matures. Size — 1 mm long. Ovary: General — Inferior. Thin epidermis with 3 locules, forming 3 carpels with axile placentation. The ovary is covered by the lobes of the sepals. Color — R.H.S. 147 A (yellow-green group).

Fragrance: None.

I claim:

1. A new and distinct variety of *Campanula* plant, substantially as herein shown and described.

* * * * *